United States Patent
Dalvi et al.

(10) Patent No.: US 9,980,904 B2
(45) Date of Patent: May 29, 2018

(54) DRY POWDER FORMULATION

(71) Applicant: Teva Branded Pharmaceutical Products R&D, Inc., Frazer, PA (US)

(72) Inventors: Mukul Dalvi, Weston, FL (US); Seah Kee Tee, Weston, FL (US)

(73) Assignee: Teva Branded Pharmaceutical Products R&D, Inc., Frazer, PA (US)

( * ) Notice: Subject to any disclaimer, the term of this patent is extended or adjusted under 35 U.S.C. 154(b) by 0 days. days.

(21) Appl. No.: 15/519,447

(22) PCT Filed: Oct. 16, 2015

(86) PCT No.: PCT/US2015/055919
§ 371 (c)(1),
(2) Date: Apr. 14, 2017

(87) PCT Pub. No.: WO2016/061448
PCT Pub. Date: Apr. 21, 2016

(65) Prior Publication Data
US 2017/0239177 A1    Aug. 24, 2017

Related U.S. Application Data

(60) Provisional application No. 62/064,690, filed on Oct. 16, 2014.

(51) Int. Cl.
| | |
|---|---|
| A61K 9/00 | (2006.01) |
| A61K 9/14 | (2006.01) |
| A61K 31/00 | (2006.01) |
| A61K 31/137 | (2006.01) |
| A61K 31/573 | (2006.01) |
| A61K 31/58 | (2006.01) |
| A61K 47/26 | (2006.01) |

(52) U.S. Cl.
CPC .......... *A61K 9/0075* (2013.01); *A61K 9/0073* (2013.01); *A61K 9/14* (2013.01); *A61K 31/00* (2013.01); *A61K 31/137* (2013.01); *A61K 31/573* (2013.01); *A61K 31/58* (2013.01); *A61K 47/26* (2013.01)

(58) Field of Classification Search
CPC ...... A61K 9/0073; A61K 9/0075; A61K 9/14; A61K 31/00; A61K 31/137; A61K 31/573; A61K 31/58; A61K 47/26
See application file for complete search history.

(56) References Cited

U.S. PATENT DOCUMENTS

| | | |
|---|---|---|
| 2005/0121027 A1 | 6/2005 | Nilsson et al. |
| 2010/0189780 A1 | 7/2010 | Walz et al. |

FOREIGN PATENT DOCUMENTS

| | | |
|---|---|---|
| EP | 0941067 A2 | 9/1999 |
| WO | 98/16205 A2 | 4/1998 |
| WO | 2005/105043 A2 | 11/2005 |

OTHER PUBLICATIONS

International Search Report for International Application No. PCT/US2015/055919, 4 pages.
Written Opinion for International Application No. PCT/US2015/055919, 6 pages.

*Primary Examiner* — Michael B. Pallay
(74) *Attorney, Agent, or Firm* — Morgan, Lewis & Bockius LLP

(57) ABSTRACT

This invention provides a process for preparing an inhalable dry powder pharmaceutical formulation comprising the step of heating a sealed wrapper containing a desiccant and an inhaler or a capsule, the inhaler or capsule further containing a dry powder formulation comprising an inhalable active pharmaceutical ingredient and a carrier, wherein the wrapper forms a barrier to the ingress of moisture and wherein heating the sealed wrapper and its contents is performed at a temperature of 30-50° C.

20 Claims, No Drawings

DRY POWDER FORMULATION

CROSS-REFERENCE TO RELATED APPLICATIONS

This application is a U.S. National Stage filing of International Patent Application No. PCT/US2015/055919 filed Oct. 16, 2015, which claims priority to U.S. Provisional Application No. 62/064,690, filed Oct. 16, 2014, the entire disclosure of each is incorporated herein by reference in their entirety for all purposes.

FIELD OF THE INVENTION

This invention relates to a dry powder formulation and particularly to a process for equilibrating a dry powder formulation.

BACKGROUND OF THE RELATED ART

The present invention is directed to the provision of a dry powder formulation containing one or more active pharmaceutical ingredients (APIs) for the treatment of respiratory disorders such as asthma or COPD. A range of classes of medicaments have been developed to treat respiratory disorders and each class has differing targets and effects. A common feature of inhalable medicaments is that they must penetrate deep into the lung in order to reach their site of action.

To this end, the APIs are micronised, e.g. by jet milling, in order to obtain particles having the required size, typically a mass median aerodynamic diameter (MMAD) of 1-5 μm. The micronisation process imparts energy into the particles of the API, leading to fracture and particle size reduction. This process generates new surfaces which are high in energy and possess static charge. The energy imparted by the micronisation process may also lead to the introduction of amorphous character into the otherwise crystalline material of the API particles. These activated surfaces are generally regarded in the art as being undesirable, primarily because they have a tendency to absorb water leading to agglomeration of the API particles. This unpredictably detrimentally affects the particle size distribution of the API which in turn affects the amount of fine particles of API reaching the lungs, quantified by the fine particle fraction (FPF), as determined using an impactor.

Various post-micronisation techniques have been proposed to relax and equilibrate the powder prior to formulation in order achieve a more consistent performance (principally a consistent FPF). They typically involve exposing the micronised particles to a humid environment. See, for example, the discussion of this approach in Particulate Interactions in Dry Powder Formulations for Inhalation, X. M. Zeng et al., Taylor & Francis, London, 2000.

However, post-micronisation treatment adds to the complexity of the process and delays the manufacturing and packaging processes. There remains a need in the art for improved approaches.

BRIEF SUMMARY OF THE INVENTION

Accordingly, the present invention provides a process for preparing an inhalable dry powder pharmaceutical formulation comprising the step of: heating a sealed wrapper containing a desiccant and an inhaler or a capsule, the inhaler or capsule further containing a dry powder formulation comprising an inhalable active pharmaceutical ingredient and a carrier, wherein the sealed wrapper forms a barrier to the ingress of moisture and wherein heating the sealed wrapper and its contents is performed at a temperature of 30-50° C.

DETAILED DESCRIPTION OF CERTAIN EMBODIMENTS OF THE INVENTION

The present invention provides a simplified and hence more efficient process for preparing the inhalation product. Dry powder formulations are presented to the end user either in a dry powder inhaler, or in capsules. The inhaler or capsules is or are often supplied within a sealed wrapper, usually made of foil, to keep the product protected from moisture. The present inventors have found that the sealed product may be heat treated to condition the API and then presented to the supply chain for provision to the end user, without further processing. This is a significant advantage, by reducing the cost and complexity of the manufacturing process.

The inhalable dry powder pharmaceutical formulation comprises an inhalable API and a carrier. There may be one or more APIs present, i.e. the product may be a monoproduct or a combination product.

The API is preferably a bronchodilator and/or an inhaled glucocorticosteroid. Bronchodilators are employed to dilate the bronchi and bronchioles, decreasing resistance in the airways, thereby increasing the airflow to the lungs. Bronchodilators may be short-acting or long-acting. Short-acting bronchodilators provide a rapid relief from acute bronchoconstriction, whereas long-acting bronchodilators help control and prevent longer-term symptoms. Different classes of bronchodilators target different receptors in the airways. Two commonly used classes are $\beta_2$-agonists and anticholinergics.

$\beta_2$-Adrenergic agonists (or "$\beta_2$-agonists") act upon the $\beta_2$-adrenoceptors which induces smooth muscle relaxation, resulting in dilation of the bronchial passages. Examples of long-acting $\beta_2$-agonists (LABAs) include formoterol (fumarate), salmeterol (xinafoate), indacaterol (maleate), carmoterol (hydrochloride) and vilanterol (trifenatate). Examples of short-acting $\beta_2$-agonists (SABAs) include salbutamol (sulfate), terbutaline (sulfate), pirbuterol (acetate) and metaproterenol (sulfate).

Anticholinergics (also known as antimuscarinics) block the neurotransmitter acetylcholine by selectively blocking its receptor in nerve cells. On topical application, anticholinergics act predominantly on the $M_3$ muscarinic receptors located in the airways to produce smooth muscle relaxation, thus producing a bronchodilatory effect. Examples of long-acting muscarinic antagonists (LAMAs) include tiotropium (bromide), aclidinium (bromide), glycopyrronium (bromide), Umeclidinium (bromide), oxybutynin (xinafoate, hydrochloride or hydrobromide) and darifenacin (hydrobromide).

Another class of medicaments employed in the treatment of respiratory disorders are inhaled corticosteroids (ICSs). ICS are steroid hormones used in the long-term control of respiratory disorders. They function by reducing the airway inflammation. Examples include budesonide, beclomethasone (dipropionate), mometasone (furoate) and fluticasone (propionate or furoate).

The API is preferably an inhaled glucocorticosteroid, a $\beta_2$-agonist, an anticholinergic agent or a combination thereof, more preferably an inhaled glucocorticosteroid in combination with a $\beta_2$-agonist, and most preferably a combination of fluticasone and salmeterol, or budesonide and formoterol, including pharmaceutically acceptable salts or solvates thereof.

A dry powder formulation typically contains a micronised active ingredient and a coarse carrier. The active ingredient needs to be in micronised form (typically a mass median aerodynamic diameter of 1-5 μm, more typically 2-4 μm). This size of particle is able to penetrate the lung on inhalation. However, such particles have a high surface energy and require a coarse carrier in order to be able to meter the formulation. Examples of particulate carriers include lactose, glucose, or sodium starch glycolate, preferably lactose and most preferably α-lactose monohydrate. The coarse carrier particles are of a size that, after inhalation, most of them remain in the inhaler or deposit in the mouth and upper airways. Accordingly, the carrier preferably has a volume mean diameter (VMD) of 40 microns or more, more preferably the carrier particles have a VMD of 50-250 microns. The particle size may be determined using laser light scattering with laser diffraction system, e.g. from Sympatec GmbH, Claasthal-Zellerfeld, Germany.

The formulation is provided in an inhaler or a capsule.

The dry powder formulation may be presented in an inhaler, e.g. in the reservoir of a multi-dose dry powder inhaler (MDPI), for example the inhalers sold under the brand name Spiromax® and the inhalers described in WO 92/10229 and WO 2011/054527. Such inhalers comprise a chassis, a dosing chamber, a mouthpiece and the medicament. The formulation may also be presented in a blister strip of unit doses within the inhaler, such as the dry powder nebuliser from MicroDose Therapeutx Inc. and the inhalers described in WO 2005/081833 and WO 2008/106616.

The dry powder formulation may alternatively be metered and filled into capsules, e.g. gelatin or hydroxypropyl methylcellulose capsules, such that the capsule contains a unit dose of active ingredient. When the dry powder is in a capsule containing a unit dose of active ingredient, the total amount of composition will depend on the size of the capsules and the characteristics of the inhalation device with which the capsules are being used.

The inhaler or capsules is or are sealed within a sealed wrapper. In a preferred embodiment, the sealed wrapper contains the desiccant and inhaler or capsule and nothing else. Such wrappers are well known in the art. They are typically comprised of aluminium foil, and may be a laminate in which at least one of the layers is aluminium foil. The laminates are multi-layer materials containing layers of aluminium foil and layers of plastics materials, such as polyethylene terephthalate (PET), polyamide, e.g. oriented polyamide (oPA) and polyethylene, e.g. low density polyethylene (PE-LD). The layers are adhered using an adhesive, such as a polyurethane adhesive. The wrapper tends to have a total weight of 50-300 g/sqm, more preferably 100-200 g/sqm. The sealed wrapper forms a barrier to the ingress of moisture.

The sealed wrapper further contains a desiccant. The desiccant is preferably presented in a separate packet within the space defined by the sealed wrapper. The desiccant may be silica gel, molecular sieves, clay, activated carbon, or combinations thereof. Preferably the desiccant is silica gel. The packaging for the desiccant packet is preferably formed of HDPE fibres. Desiccant packets are commercially available, e.g. MiniPax® Sorbent Packets from Multisorb Technologies.

The sealed wrapper and its contents are heated and it has been found that this heating step improves the performance of the inhalable formulation. It is believed that the heating step works by equilibrating the surface post-micronisation. It is surprising that heating is effective within the confines of the sealed wrapper as the formulation is not exposed to a humid environment under these conditions.

Heating is performed at a temperature of 30-50° C., more preferably at a temperature of 35-45° C., and most preferably at a temperature of 38-42° C. The heating step is a conditioning step for the API, in order to equilibrate the surface and reduce the amorphous content of the API.

The heating step is preferably conducted for 1 day to 6 weeks, more preferably 1-3 weeks and most preferably for 2 weeks.

No other conditioning step is required. An initial conventional conditioning step may be applied, but it is not required. Preferably, the heating step according to the present invention is the sole post-micronisation treatment step.

Since the formulation is present in a sealed wrapper, the humidity of the heating step is less relevant. Preferably the relative humidity is less than 60% (i.e. 0-60%), more preferably 0-40% and most preferably 0-20%.

The present invention will now be described with reference to the accompanying examples, which are not intended to be limiting.

Examples

Equilibration Studies
Study 1. Two batches of fluticasone/salmeterol housed within a Spiromax® device were prepared. Combination batches of fluticasone propionate and salmeterol xinafoate were selected at two different strengths 25 μg/25 μg and 100 μg/25 μg, respectively. Each batch was divided into two and equilibrated for six weeks under the conditions specified by each protocol.
Protocol 1: 30° C./65% RH (unwrapped)
Protocol 2: 40° C. (wrapped in foil with desiccant)
Following inhaler equilibration, aerodynamic particle size distribution analyses (measuring FPF and FPD) were performed at intervals of 0, 2, 3, 4 and 6 weeks.
Study 2. Two batches of fluticasone/salmeterol housed within a Spiromax® device were prepared. Combination batches of fluticasone propionate and salmeterol xinafoate were selected at two different strengths, as in study 1. Each batch was divided into two and equilibrated for six weeks under the conditions specified by each protocol.
Protocol 1: 30° C./65% RH (unwrapped)
Protocol 3: 40° C. (wrapped in foil with desiccant)
During inhaler equilibration, aerodynamic particle size distribution analyses (measuring FPF and FPD) were performed at intervals of 0, 2, 3, 4 and 6 weeks.
Results
The results of the equilibration studies are shown in Table 1.

TABLE 1

Degradation in aerodynamic particle size distribution.
Results shown display Study 1 (after 6 week equilibration)
and Study 2 (during 6 week equilibration).

| Study no. | Batch (μg) | Protocol | Drug fraction analysed | Aerodynamic particle size distribution (% change from base) | |
|---|---|---|---|---|---|
| | | | | FPD | FPF |
| 1 | 25/25 | 30° C./65% RH (unwrapped) | Fluticasone propionate (Fp) | −16 | −19 |
| | | | Salmeterol | −20 | −19 |

TABLE 1-continued

Degradation in aerodynamic particle size distribution.
Results shown display Study 1 (after 6 week equilibration)
and Study 2 (during 6 week equilibration).

| Study no. | Batch (µg) | Protocol | Drug fraction analysed | Aerodynamic particle size distribution (% change from base) FPD | FPF |
|---|---|---|---|---|---|
| | | | xinafoate (Sx) | | |
| 1 | 25/25 | 40° C. (wrapped) | Fp | −13 | −12 |
| | | | Sx | −2 | −2 |
| 1 | 100/25 | 30° C./65% RH (unwrapped) | Fp | −13 | −12 |
| | | | Sx | −9 | −10 |
| 1 | 100/25 | 40° C. (wrapped) | Fp | −17 | −14 |
| | | | Sx | 0 | 0 |
| 2 | 25/25 | 30° C./65% RH (unwrapped) | Fp | −19 | −16 |
| | | | Sx | −20 | −18 |
| 2 | 25/25 | 40° C. (wrapped) | Fp | −13 | −12 |
| | | | Sx | −2 | −2 |
| 2 | 100/25 | 30° C./65% RH (unwrapped) | Fp | −12 | −12 |
| | | | Sx | −9 | −10 |
| 2 | 100/25 | 40° C. (wrapped) | Fp | −16 | −14 |
| | | | Sx | 0 | 0 |

Formulation Stability Testing

Study 3. Following inhaler equilibration according to protocol 2 (six weeks at 40° C./75% RH wrapped in foil with desiccant), eight-week stability tests of fluticasone propionate and salmeterol xinafoate (25 µg/25 µg and 100 µg/25 µg) were conducted. The in-use stability testing was conducted at 30° C./65% RH (unwrapped) as per discussion with the FDA.

Aerodynamic particle size distribution analyses (measuring FPF and FPD) were performed at intervals of 0, 2, 4 and 8 weeks.

Study 4. Following inhaler equilibration according to protocol 3 (six weeks at 40° C. wrapped in foil with desiccant), six-month stability tests of fluticasone propionate and salmeterol xinafoate (25 µg/25 µg and 100 µg/25 µg) were conducted. The stability of the formulations was assessed following storage under two different condition sets.

Condition set 1: 40° C. (wrapped in foil with desiccant)
Condition set 2: 25° C./60% RH (wrapped in foil with desiccant)

Aerodynamic particle size distribution analyses (measuring FPF and FPD) were performed at intervals of 0, 3 and 6 months.

Results
The results are set out in Tables 2 and 3

TABLE 2

Eight week in-use stability study.

| Study no. | Batch (µg) | Protocol | Drug fraction analysed | Aerodynamic particle size distribution (% change from base) FPD | FPF |
|---|---|---|---|---|---|
| 3 | 25/25 | 30° C./65% RH (unwrapped) | Fp | −10 | −9 |
| | | | Sx | −17 | −14 |
| 3 | 100/25 | 30° C./65% RH (unwrapped) | Fp | 0 | 0 |
| | | | Sx | −4 | −3 |

TABLE 3

Six month stability study.

| Study no. | Batch | Protocol | Drug fraction analysed | Aerodynamic particle size distribution (% change from base) FPD | FPF |
|---|---|---|---|---|---|
| 4 | 25/25 | 25° C./60% RH (wrapped) | Fp | −4 | 0 |
| | | | Sx | −5 | 0 |
| 4 | 25/25 | 40° C. (wrapped) | Fp | −9 | −6 |
| | | | Sx | −9 | −4 |
| 4 | 100/25 | 25° C./60% RH (wrapped) | Fp | 0 | 0 |
| | | | Sx | −3 | −1 |
| 4 | 100/25 | 40° C. (wrapped) | Fp | −8 | −6 |
| | | | Sx | −13 | −9 |

The invention claimed is:

1. A process for preparing an inhalable dry powder pharmaceutical formulation comprising the step of heating a sealed wrapper containing a desiccant and an inhaler or a capsule, the inhaler or capsule further containing a dry powder formulation comprising an inhalable active pharmaceutical ingredient and a carrier, wherein the sealed wrapper forms a barrier to the ingress of moisture and wherein heating the sealed wrapper and its contents is performed at a temperature of 30-50° C.

2. The process as claimed in claim 1, wherein the heating is performed at a temperature of 38-42° C.

3. The process as claimed in claim 1, wherein the heating is performed at a relative humidity of less than 60%.

4. The process as claimed in claim 1, wherein the heating is performed for 1 day to 6 weeks.

5. The process as claimed in claim 1, wherein the inhalable active pharmaceutical ingredient is an inhaled glucocorticosteroid, a $\beta_2$-agonist, an anticholinergic agent or a combination thereof.

6. The process as claimed in claim 5, wherein the inhalable active pharmaceutical ingredient is an inhaled glucocorticosteroid in combination with a $\beta_2$-agonist.

7. The process as claimed in claim 6, wherein the inhalable active pharmaceutical ingredient is a combination of fluticasone and salmeterol, including pharmaceutically acceptable salts or solvates thereof.

8. The process as claimed in claim 6, wherein the inhalable active pharmaceutical ingredient is a combination of budesonide and formoterol, including pharmaceutically acceptable salts or solvates thereof.

9. The process as claimed in claim 1, wherein the desiccant is silica gel.

10. The process as claimed in claim 1, wherein the sealed wrapper comprises aluminium foil.

11. The process as claimed in claim 9, wherein the sealed wrapper is a laminate in which at least one of the layers is aluminium foil.

12. The process as claimed in claim 1, wherein the carrier is lactose, glucose or sodium starch glycolate.

13. The process as claimed in claim 1, wherein the carrier is α-lactose monohydrate.

14. The process as claimed in claim 1, wherein the carrier has a volume mean diameter of 40 microns or more.

15. The process as claimed in claim 1, wherein the sealed wrapper contains the desiccant and inhaler or capsule and nothing else.

16. The process as claimed in claim 1, wherein the desiccant is presented in a separate packet within the space defined by the sealed wrapper.

17. The process as claimed in claim 1, wherein the heating is performed at a temperature of 35-45° C.

18. The process as claimed in claim 1, wherein the heating is effective to reduce the amorphous content of the inhalable active pharmaceutical ingredient.

19. The process as claimed in claim 1, wherein the heating is performed for 1-3 weeks.

20. The process as claimed in claim 1, wherein the sealed wrapper is a multi-layer material containing at least one layer of aluminium foil and at least one layer of a plastics material.

* * * * *